(12) United States Patent
Amariglio et al.

US011864757B2

(10) Patent No.: US 11,864,757 B2
(45) Date of Patent: Jan. 9, 2024

(54) RELOADABLE CARTRIDGE ASSEMBLY

(71) Applicant: Lexington Medical, Inc., Billerica, MA (US)

(72) Inventors: Leon Amariglio, Lexington, MA (US); Andrew Marecki, West Boylston, MA (US)

(73) Assignee: Lexington, Medical, Inc., Bedford, MA (US)

( * ) Notice: Subject to any disclaimer, the term of this patent is extended or adjusted under 35 U.S.C. 154(b) by 0 days.

(21) Appl. No.: 17/150,505

(22) Filed: Jan. 15, 2021

(65) Prior Publication Data

US 2022/0225984 A1 Jul. 21, 2022

(51) Int. Cl.
*A61B 17/072* (2006.01)

(52) U.S. Cl.
CPC .. *A61B 17/072* (2013.01); *A61B 2017/07264* (2013.01); *A61B 2017/07271* (2013.01); *A61B 2017/07285* (2013.01)

(58) Field of Classification Search
CPC ............ A61B 17/072; A61B 17/07207; A61B 2017/07264; A61B 2017/07271; A61B 2017/07285; A61B 2017/07214; A61B 2017/07228; A61B 2017/07257; A61B 2017/07278
USPC ............................................ 227/175.1–181.1
See application file for complete search history.

(56) References Cited

U.S. PATENT DOCUMENTS

| RE28,932 E | 8/1976 | Noiles et al. |
| 4,737,608 A | 4/1988 | Jones |
| 4,978,049 A | 12/1990 | Green |
| 5,300,081 A | 4/1994 | Young et al. |
| 5,326,013 A | 7/1994 | Green et al. |
| RE34,680 E | 8/1994 | Lieser |
| 5,474,223 A | 12/1995 | Viola et al. |
| 5,489,058 A | 2/1996 | Plyley et al. |
| 5,489,292 A | 2/1996 | Tovey et al. |

(Continued)

FOREIGN PATENT DOCUMENTS

| CN | 110505845 | 11/2020 |
| EP | 1563791 | 8/2005 |

(Continued)

OTHER PUBLICATIONS

International Searching Authority., International Search Report and Written Opinion dated Jun. 18, 2018 for PCT Application No. PCT/US2018/025988 Filed Apr. 4, 2018, 9 pages.

(Continued)

*Primary Examiner* — Stephen F. Gerrity
*Assistant Examiner* — Linda J Hodge
(74) *Attorney, Agent, or Firm* — Brooks, Cameron & Huebsch, PLLC

(57) ABSTRACT

The present disclosure includes apparatuses for a reloadable cartridge assembly. An example apparatus includes a first elongated member including a staple cartridge configured to eject a number of staples and a second elongated member pivotally coupled to the first elongated member, wherein the second elongated member includes a number of pockets configured to receive and form the number of staples ejected from the staple cartridge, and wherein a furthest distal pocket of the number of pockets is less than 6 millimeters (mm) from a distal end of the second elongated member.

20 Claims, 3 Drawing Sheets

(56) References Cited

U.S. PATENT DOCUMENTS

| | | | |
|---|---|---|---|
| 5,507,426 A | 4/1996 | Young et al. | |
| 5,522,534 A | 6/1996 | Viola et al. | |
| 5,535,935 A | 7/1996 | Vidal et al. | |
| 5,562,241 A * | 10/1996 | Knodel | A61B 17/07207 227/19 |
| 5,586,711 A | 12/1996 | Plyley et al. | |
| 5,588,579 A | 12/1996 | Schnut et al. | |
| 5,758,814 A | 6/1998 | Gallagher et al. | |
| 5,762,256 A | 6/1998 | Mastri et al. | |
| 5,799,857 A | 9/1998 | Robertson et al. | |
| 5,823,066 A | 10/1998 | Huitema | |
| 5,836,503 A | 11/1998 | Ehrenfels et al. | |
| 5,865,361 A | 2/1999 | Milliman et al. | |
| 5,901,895 A | 5/1999 | Heaton et al. | |
| 6,109,500 A | 8/2000 | Alli et al. | |
| 6,281,453 B1 | 8/2001 | Uleski | |
| 6,302,798 B1 | 10/2001 | Nakaguro | |
| 6,945,444 B2 | 9/2005 | Gresham et al. | |
| 6,953,138 B1 | 10/2005 | Dworak et al. | |
| 6,957,758 B2 | 10/2005 | Aranyi | |
| 7,044,352 B2 | 5/2006 | Shelton, IV et al. | |
| 7,044,353 B2 | 5/2006 | Mastri et al. | |
| 7,097,089 B2 | 8/2006 | Marczyk | |
| 7,143,923 B2 | 12/2006 | Shelton, IV et al. | |
| 7,143,924 B2 | 12/2006 | Scirica et al. | |
| 7,168,604 B2 | 1/2007 | Milliman et al. | |
| 7,225,963 B2 | 6/2007 | Scirica | |
| 7,234,624 B2 | 6/2007 | Gresham et al. | |
| 7,303,106 B2 | 12/2007 | Milliman et al. | |
| 7,325,713 B2 | 2/2008 | Aranyi | |
| 7,364,060 B2 | 4/2008 | Milliman | |
| 7,380,695 B2 | 6/2008 | Doll et al. | |
| 7,380,696 B2 | 6/2008 | Shelton, IV et al. | |
| 7,398,907 B2 | 7/2008 | Racenet et al. | |
| 7,404,508 B2 | 7/2008 | Smith et al. | |
| 7,422,136 B1 | 9/2008 | Marczyk | |
| 7,455,208 B2 | 11/2008 | Wales et al. | |
| 7,490,749 B2 | 2/2009 | Schall et al. | |
| 7,494,038 B2 | 2/2009 | Milliman | |
| 7,516,877 B2 | 4/2009 | Aranyi | |
| 7,546,940 B2 | 6/2009 | Milliman et al. | |
| 7,611,038 B2 | 11/2009 | Racenet et al. | |
| 7,624,902 B2 | 12/2009 | Marczyk et al. | |
| 7,694,865 B2 | 4/2010 | Scirica | |
| 7,780,055 B2 | 8/2010 | Scirica et al. | |
| 7,802,712 B2 | 9/2010 | Milliman et al. | |
| 7,824,426 B2 | 11/2010 | Racenet et al. | |
| 7,832,408 B2 | 11/2010 | Shelton, IV et al. | |
| 7,837,079 B2 | 11/2010 | Holsten et al. | |
| 7,845,535 B2 | 12/2010 | Scircia | |
| 7,857,187 B2 | 12/2010 | Milliman | |
| 7,926,692 B2 | 4/2011 | Racenet et al. | |
| 7,963,431 B2 | 6/2011 | Scirica | |
| 7,967,178 B2 | 6/2011 | Scirica et al. | |
| 7,967,180 B2 | 6/2011 | Scirica | |
| 8,020,743 B2 | 9/2011 | Shelton, IV | |
| 8,061,576 B2 | 11/2011 | Cappola | |
| 8,070,036 B1 | 12/2011 | Knodel | |
| 8,123,101 B2 | 2/2012 | Racenet et al. | |
| 8,136,712 B2 | 3/2012 | Zingman | |
| 8,141,763 B2 | 3/2012 | Milliman | |
| 8,157,148 B2 | 4/2012 | Scirica | |
| 8,235,274 B2 | 8/2012 | Cappola | |
| 8,292,157 B2 | 10/2012 | Smith et al. | |
| 8,328,822 B2 | 12/2012 | Huitema et al. | |
| 8,336,751 B2 | 12/2012 | Scirica | |
| 8,336,754 B2 | 12/2012 | Cappola et al. | |
| 8,342,378 B2 | 1/2013 | Marczyk | |
| 8,360,296 B2 | 1/2013 | Zingman | |
| 8,413,868 B2 | 4/2013 | Cappola | |
| 8,424,736 B2 | 4/2013 | Scirica et al. | |
| 8,573,460 B2 | 11/2013 | Cappola | |
| 8,573,463 B2 | 11/2013 | Scirica | |
| 8,608,043 B2 | 12/2013 | Scirica | |
| 8,622,894 B2 | 1/2014 | Banik et al. | |
| 8,684,247 B2 | 4/2014 | Scirica et al. | |
| 8,684,249 B2 | 4/2014 | Racenet et al. | |
| 8,695,865 B2 | 4/2014 | Smith et al. | |
| 8,888,814 B2 | 11/2014 | Cappola | |
| 8,910,847 B2 | 12/2014 | Nalagatla et al. | |
| 9,204,876 B2 | 12/2015 | Cappola et al. | |
| 9,364,218 B2 | 6/2016 | Scirica | |
| 9,393,016 B2 | 7/2016 | Scirica et al. | |
| 9,539,006 B2 | 1/2017 | Collings et al. | |
| 9,655,617 B2 | 5/2017 | Cappola | |
| 9,861,358 B2 | 1/2018 | Marczyk et al. | |
| 9,931,739 B2 | 4/2018 | Nelson | |
| 10,383,634 B2 | 8/2019 | Shelton, IV | |
| 2001/0030219 A1 | 10/2001 | Green et al. | |
| 2004/0232199 A1 | 11/2004 | Shelton, IV et al. | |
| 2005/0006429 A1 | 1/2005 | Wales | |
| 2006/0111210 A1 | 5/2006 | Hinman | |
| 2007/0125826 A1 | 6/2007 | Shelton, IV | |
| 2007/0262116 A1 | 11/2007 | Hueil et al. | |
| 2008/0083810 A1 | 4/2008 | Marczyk | |
| 2008/0179374 A1 | 7/2008 | Beardsley et al. | |
| 2009/0062614 A1 | 3/2009 | Adzich et al. | |
| 2009/0145947 A1 | 6/2009 | Scirica et al. | |
| 2009/0272614 A1 | 11/2009 | Watarai | |
| 2010/0264193 A1 | 10/2010 | Huang et al. | |
| 2011/0062211 A1 | 3/2011 | Ross | |
| 2011/0084113 A1 | 4/2011 | Bedi et al. | |
| 2011/0089221 A1 * | 4/2011 | Masiakos | A61B 17/07207 227/180.1 |
| 2011/0253765 A1 | 10/2011 | Nicholas | |
| 2012/0181322 A1 * | 7/2012 | Whitman | A61B 17/068 227/176.1 |
| 2012/0286019 A1 | 11/2012 | Hueil | |
| 2013/0092719 A1 | 4/2013 | Kostrzewski | |
| 2013/0098966 A1 | 4/2013 | Kostrzewski et al. | |
| 2013/0199327 A1 | 8/2013 | Park et al. | |
| 2013/0245676 A1 | 9/2013 | Cappola | |
| 2013/0304115 A1 | 11/2013 | Miyamoto | |
| 2014/0276949 A1 | 9/2014 | Staunton et al. | |
| 2015/0150620 A1 * | 6/2015 | Miyamoto | A61B 18/1445 227/176.1 |
| 2015/0196996 A1 | 7/2015 | Nelson | |
| 2015/0342605 A1 | 12/2015 | Abbott et al. | |
| 2015/0374396 A1 | 12/2015 | Strobl | |
| 2016/0166250 A1 | 6/2016 | Marczyk | |
| 2016/0270786 A1 | 9/2016 | Scirica | |
| 2017/0000485 A1 | 1/2017 | Shelton, IV et al. | |
| 2017/0172577 A1 | 6/2017 | Wenchell et al. | |
| 2017/0281177 A1 | 10/2017 | Harris et al. | |
| 2017/0281184 A1 | 10/2017 | Shelton, IV | |
| 2017/0281220 A1 | 10/2017 | Hibner | |
| 2018/0078354 A1 | 3/2018 | Cardinale et al. | |
| 2018/0168572 A1 | 6/2018 | Burbank | |
| 2018/0168599 A1 | 6/2018 | Bakos | |
| 2018/0289370 A1 | 10/2018 | Amariglio et al. | |
| 2018/0310935 A1 | 11/2018 | Wixey | |
| 2018/0317915 A1 | 11/2018 | McDonald, II | |
| 2018/0368832 A1 | 12/2018 | Marecki et al. | |
| 2018/0368839 A1 * | 12/2018 | Shelton, IV | B23K 26/21 |
| 2019/0000472 A1 * | 1/2019 | Shelton, IV | A61B 17/07207 |
| 2020/0008801 A1 | 1/2020 | Somekh et al. | |
| 2020/0015818 A1 | 1/2020 | Amariglio et al. | |
| 2020/0015822 A1 | 1/2020 | Marczyk et al. | |
| 2020/0085433 A1 | 3/2020 | Aranyi | |
| 2020/0093486 A1 | 3/2020 | Somekh et al. | |
| 2020/0222046 A1 | 7/2020 | Somekh et al. | |
| 2021/0007740 A1 | 1/2021 | Marecki et al. | |
| 2021/0275168 A1 * | 9/2021 | Smith | A61B 17/0686 |

FOREIGN PATENT DOCUMENTS

| | | |
|---|---|---|
| EP | 1563792 | 8/2005 |
| EP | 1563794 | 8/2005 |
| EP | 1709911 | 10/2006 |
| EP | 1021130 | 11/2006 |
| EP | 2253277 | 11/2010 |
| EP | 2253278 | 11/2010 |
| EP | 2886020 | 6/2015 |
| EP | 2484290 | 7/2015 |

(56) References Cited

FOREIGN PATENT DOCUMENTS

| | | |
|---|---|---|
| EP | 2311385 | 5/2017 |
| EP | 3606446 | 2/2020 |
| EP | 3641665 | 4/2020 |
| WO | 2018/187399 | 10/2018 |
| WO | 2018/237223 | 12/2018 |
| WO | 2020/010091 | 1/2020 |
| WO | 2020/150360 | 7/2020 |

OTHER PUBLICATIONS

International Searching Authority., International Search Report and Written Opinion dated Oct. 22, 2018 for PCT Application No. PCT/US2018/038909, Filed Jun. 22, 2018, 10 pages.

International Searching Authority., International Search Report and Written Opinion dated Oct. 4, 2019 for PCT Application No. PCT/US2019/040315 Filed Jul. 2, 2019, 9 pages.

International Searching Authority., International Search Report and Written Opinion dated Mar. 25, 2022 for PCT Application No. PCT/US2022/012342 Filed Jan. 13, 2022, 11 pages.

* cited by examiner

RELOADABLE CARTRIDGE ASSEMBLY

TECHNICAL FIELD

The present disclosure relates generally to a reloadable cartridge assembly of a surgical stapler.

BACKGROUND

A reloadable cartridge assembly can be used in a number of surgical devices. One example includes use as a surgical stapler. A surgical stapler is a fastening device used to clamp tissue between opposing jaw structures to join tissue using surgical fasteners. A reloadable cartridge can include two elongated members used to clamp the tissue. One of the elongated members can include one or more reloadable cartridges and the other elongated member can include an anvil that can be used to form a staple when driven from the reloadable cartridge. A surgical stapler can receive one or more reloadable cartridges. An example of reloadable cartridges can include having rows of staples having a linear length. A row of staples can have a linear length between 30 mm and 60 mm, for example. A staple can be ejected by actuation of a movable handle member that is a part of a surgical handle assembly of the surgical stapler.

DETAILED DESCRIPTION

Figure 1:
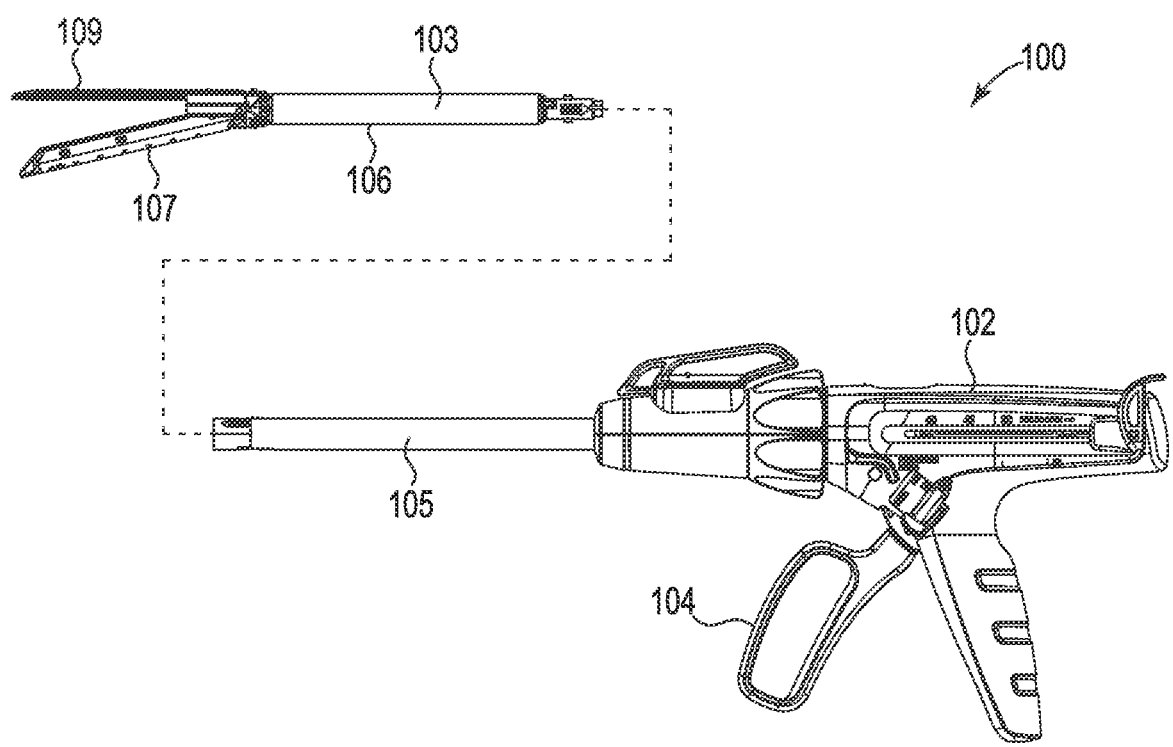
FIG. 1 is a schematic diagram of a surgical stapler including a surgical handle assembly and a reloadable cartridge assembly in an unclamped position in accordance with a number of embodiments of the present disclosure.

The present disclosure includes apparatuses for a reloadable cartridge assembly. An example apparatus includes a first elongated member including a staple cartridge configured to eject a number of staples and a second elongated member pivotally coupled to the first elongated member, wherein the second elongated member includes a number of pockets configured to receive and form the number of staples ejected from the staple cartridge, and wherein a furthest distal pocket of the number of pockets is less than 6 millimeters (mm) from a distal end of the second elongated member. In some examples, the furthest distal pocket of the number of pockets can be less than 2 mm from the distal end of the second elongated member.

During use of a surgical stapler with a surgical handle assembly coupled to a reloadable cartridge, the elongated members (e.g., jaws) of the reloadable cartridge assembly can be moved to a clamped position in response to a toothed rack or other structure being moved in a linear distal direction in response to a moveable handle of the surgical handle assembly being moved in a proximal direction. The reloadable cartridge assembly can advance to an unclamped position in response to the toothed rack being moved in the linear proximal direction. Once in a clamped position, the staples can be delivered by continued advancement of the toothed rack in a linear distal direction.

In a number of embodiments, the surgical handle assembly with the surgical stapler coupled to the reloadable cartridge assembly can deploy a number of staples. The reloadable cartridge assembly can deploy the number of staples in response to a user changing the mode of the surgical stapler from clamp/unclamp to staple and moving the movable handle member in the proximal direction.

In some examples, the surgical stapler can be an endoscopic stapler for general, abdominal, gynecologic, pediatric, and/or thoracic surgery. The surgical stapler can be utilized for resection, transection, and/or creation of anastomoses, for example.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

It is to be understood that the terminology used herein is for the purpose of describing particular embodiments only and is not intended to be limiting. As used herein, the singular forms "a", "an", and "the" can include both singular and plural referents, unless the context clearly dictates otherwise. In addition, "a number of", "at least one", and "one or more" (e.g., a number of pockets) can refer to one or more pockets, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to". The terms "coupled" and "coupling" mean to be directly or indirectly connected physically or for access to and movement of the movable handle member, as appropriate to the context.

The figures herein follow a numbering convention in which the first digit or digits correspond to the figure number and the remaining digits identify an element or component in the figure. Similar elements or components between different figures may be identified by the use of similar digits. For example, 106 may reference element "6" in FIG. 1, and a similar element may be referenced as 206 in FIG. 2A. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1 is a schematic diagram of a surgical stapler 100 including a surgical handle assembly 102 and a reloadable cartridge assembly 103 in an unclamped position in accordance with a number of embodiments of the present disclosure. As shown in the example of FIG. 1, the reloadable cartridge assembly 103 (e.g. a disposable loading unit) can be releasably secured to a distal end of an elongated body of the surgical handle assembly 102 via shaft 106.

In this example, the reloadable cartridge assembly 103 can include a first elongated member 107 and a second elongated member 109. The reloadable cartridge assembly 103 can be in a clamped position when the first elongated member 107 and the second elongated member 109 are clamping tissue, proximate to each other, and/or contacting each other. The reloadable cartridge assembly 103 can be in an unclamped position when the first elongated member 107 and the second elongated member 109 are not clamping tissue, receiving tissue, and/or are not in contact with each other.

In a number of embodiments, the first elongated member 107 can house one or more staple cartridges. The second elongated member can have an anvil that can be used to form a staple when driven from the staple cartridge. As mentioned, a reloadable cartridge assembly 103 can receive reloadable cartridge assemblies having rows of staples.

The surgical handle assembly 102 coupled to the reloadable cartridge assembly 103 can advance the reloadable cartridge assembly 103 to the clamped position in response to the user actuating the movable handle member 104 of the surgical handle assembly 102 in a proximal direction. A shaft of the surgical handle assembly 102 can interface with a drive mechanism included in the reloadable cartridge assembly 103 when the surgical handle assembly 102 and the reloadable cartridge assembly 103 are connected. Distal movement of the drive mechanism in response to the user actuating the movable handle member 104 in the proximal direction can move an I-beam distally. The I-beam can be included in the reloadable cartridge assembly 103 and can actuate the first elongated member 107 and/or the second elongated member 109. The I-beam can move the reloadable cartridge assembly 103 to the clamped position in response to the I-beam moving in the distal direction.

The user can also advance the reloadable cartridge assembly 103 to the unclamped position in response to the user actuating the movable handle member 104 in a distal direction. Proximal movement of the drive mechanism in response to the user actuating the movable handle member 104 in the distal direction can move the I-beam distally and accordingly, the I-beam can move the reloadable cartridge assembly 103 to the unclamped position in response to the I-beam moving in the proximal direction.

In a number of embodiments, the surgical handle assembly 102 coupled to the reloadable cartridge assembly 103 can deploy a number of staples. The reloadable cartridge assembly 103 can deploy the number of staples in response to the user moving the movable handle member 104 to the most proximal position after a user changes the mode of the stapler from clamp/unclamp to staple. For example, further movement of the I-beam in the distal direction can cause a mechanism included in the first elongated member 107 to eject a number of staples and/or a blade to move towards a distal end (e.g., distal end 224 in FIGS. 2A and 2B) of a first slot (e.g., first slot 218 in FIG. 2A) of the second elongated member 109 and/or a distal end of a second slot of the first elongated member 107.

In some examples, a distal end of the surgical stapler 100 can be inserted into a body of a patient or through a trocar or similar devices when the reloadable cartridge assembly 103 is in a clamped position. Once the distal end of the surgical stapler 100 is positioned in the body of the patient, the user can release or move the movable handle member 104 to a distal position to place the reloadable cartridge assembly 103 into an unclamped position. The user can position the reloadable cartridge assembly to place tissue between the first elongated member 107 and the second elongated member 109 and move the movable handle member 104 to a proximal position to move the reloadable cartridge assembly to the clamped position again and clamp the tissue.

In a number of embodiments herein, the surgical handle assembly 102 is shown as being manually actuated. Other handle assemblies such as ones that are driven by an electric motor may also be used. In these motor driven handle assemblies, a disposable or reusable/rechargeable battery may be used. It is also envisioned that the handle assembly could be replaced by a robotic or remotely controlled mechanism. In this embodiment, the physician/user is remote from the patient and controls the device from a computer input station or the like. In this embodiment, the reload cartridge assembly 103 could be connected to a robotic or remotely controlled arm.

In some examples, the reloadable cartridge assembly 103 is shown to include a connection to the surgical handle assembly 102 which allows the distal end of the reloadable cartridge assembly 103 to be clamped and/or unclamped. The embodiments described herein are equally applicable to a configuration wherein the surgical handle assembly 102 comprises the reloadable cartridge assembly 103. In various embodiments, the reloadable cartridge assembly 103 could comprise a connector and the elongated members 107 and 109 or just a staple cartridge configured to be removably positioned in one of the elongated members 107 and 109.

Figure 2A:
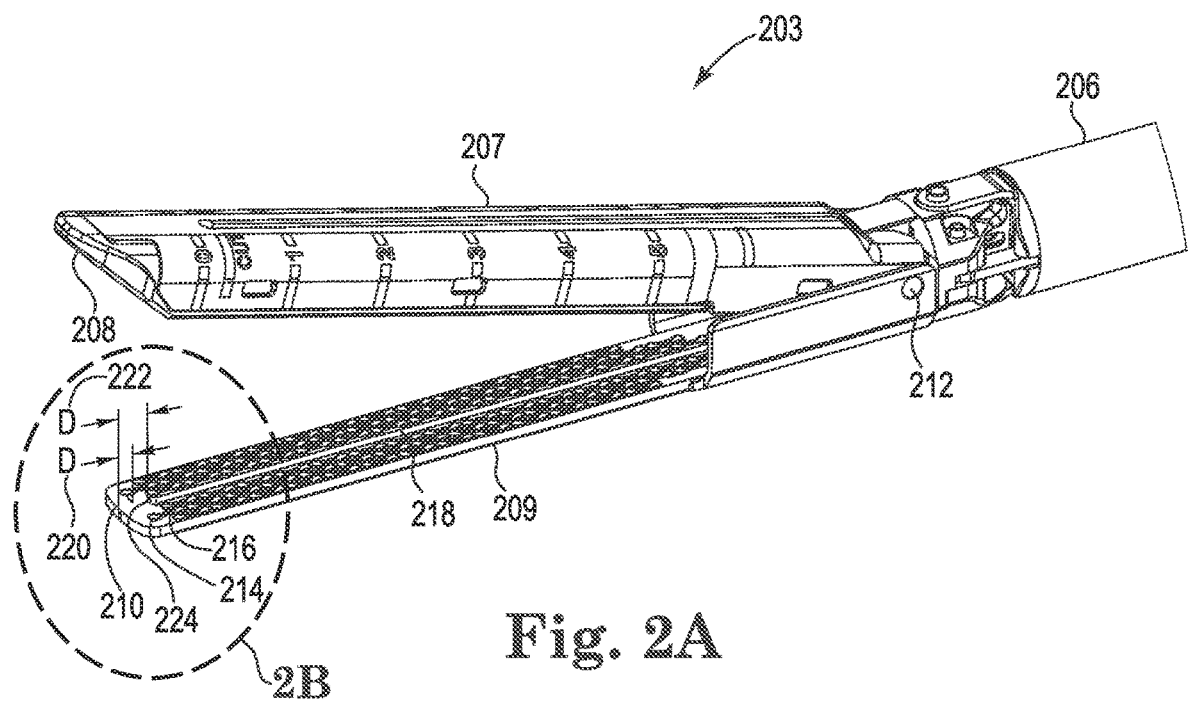
FIG. 2A is a schematic diagram of a reloadable cartridge assembly in an unclamped position in accordance with a number of embodiments of the present disclosure.

FIG. 2A is a schematic diagram of a reloadable cartridge assembly 203 in an unclamped position in accordance with a number of embodiments of the present disclosure. The reloadable cartridge assembly 203 can include a shaft 206, a first elongated member 207, a second elongated member 209, and a pin 212.

A proximal end of the first elongated member 207 can be pivotally coupled to a proximal end of the second elongated member 209. In some examples, the first elongated member 207 and the second elongated member 209 can be pivotally coupled via pin 212. A distal end of shaft 206 can be coupled to the proximal end of the first elongated member 207 and/or the second elongated member 209.

In a number of embodiments, a distal end 208 of the first elongated member 207 and/or a distal end 210 of the second elongated member 209 can be blunt. Damage to adjacent tissue and/or organs can be avoided when the distal end 208 of the first elongated member 207 is blunt and/or when the distal end 210 of the second elongated member 209 is blunt. For example, distal end 208 and/or distal end 210 can be substantially perpendicular to other sides of the first and/or second elongated members 207 and 209. In some examples, distal end 208 and/or distal end 210 can be coupled to other sides of the first and/or second elongated members 207 and 209 via smooth (e.g., rounded) surfaces.

Figure 2B:
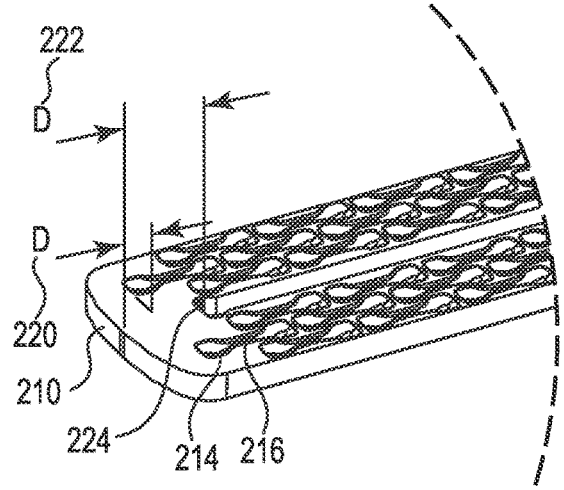
FIG. 2B is a schematic diagram of a portion of a reloadable cartridge assembly in an unclamped position in accordance with a number of embodiments of the present disclosure.

The first elongated member 207 can house a staple cartridge including a number of staples and/or a mechanism configured to eject the number of staples when the reloadable cartridge assembly 203 is in a clamped position. As illustrated in FIGS. 2A and 2B, the second elongated member 209 can include a number of pockets 214 and/or a number of grooves 216. A groove of the number of grooves 216 can create an opening from a first pocket of the number of pockets 214 to a second pocket of the number of pockets 214. In some examples, pairs of pockets of the number of pockets 214 and a groove of the number of grooves 216 can run parallel to a longitudinal axis of the second elongated member 209.

The number of pockets 214 and/or the number of grooves can be configured to receive and form the number of staples ejected from the staple cartridge. For example, a first pocket of the number of pockets 214 can be configured to receive a first portion of a staple of the number of staples, a second pocket of the number of pockets 214 can be configured to receive a second portion of the staple, and a groove of the number of grooves 216 can be configured to receive and fold the first portion and the second portion of the staple. In some examples, the first portion of the staple can be a first leg of a staple, the second portion of the staple can be a second leg, and a third portion of the staple can be a crown that couples the first leg to the second leg. As the staple is ejected from the staple cartridge, the first leg and the second leg are each received in a pocket of the number of pockets 214 and then are bent towards each other in a groove of the number of grooves 216.

In a number of embodiments, the furthest distal pocket of the number of pockets 214 can be a distance 220 from a distal end 210 of the second elongated member 209. Distance 220 can be 6 mm, 4 mm, or 2 mm, or less, for example. Distance 220 can be zero, however, to have adequate tissue compression to ensure optimal staple formation, distance 220 may be greater than zero.

Often positioning a reloadable cartridge assembly 203 within a body of a patient can be difficult because an organ and/or tissue to be transected can be close to or touching adjacent organs and/or tissue. In some examples, reducing distance 220 between the furthest distal pocket of the number of pockets 214 and the distal end 210 of the second elongated member 209 can improve clinical outcomes. For example, when distance 220 is minimized (e.g., the furthest distal pocket of the number of pockets 214 is near the distal end 210 of the second elongated member 209), the user can determine the most distal staple will be ejected very close to the distal end of the elongated member. Accordingly, the user can more accurately place the number of staples in tissue and/or organs and avoid placing staples in the wrong tissue and/or organs.

Reducing the distance 220 between the furthest distal pocket of the number of pockets 214 and the distal end 210 of the second elongated member 209 can also reduce damage to adjacent tissue and/or organs that may occur as a result of the user needing to place the reloadable cartridge assembly 203 further into the patient's body or further into adjacent tissue and/or organs. To properly place the number staples at the desired location in the body, the user may need to go a further distance into the body and/or into adjacent tissue and/or organs of the patient if the distance 220 is a greater distance. For example, when transecting a stomach, a spleen, a diaphragm, and/or a duodenum may be contacting or adjacent to the stomach. If distance 220 is reduced, there may be less chance of the second elongated member 209 contacting the spleen, diaphragm, and/or the duodenum and/or less surface area on the spleen, diaphragm, and/or the duodenum contacted by the second elongated member 209.

As illustrated in FIG. 2A, the second elongated member 209 can include a first slot 218. Although not illustrated in FIG. 2A, the first elongated member 207 can include a second slot. First slot 218 of the second elongated member 209 and/or the second slot of the first elongated member can receive a blade to cut tissue in response to and/or simultaneously to the number of staples being ejected from the staple cartridge when the reloadable cartridge assembly 203 is in the clamped position.

A distal end 224 of the first slot 218 can be a distance 222 from the distal end 210 of the second elongated member 209. Distance 222 can be 8 mm, 6 mm, or 4 mm or less. In some examples, distance 222 can be at least partially based on distance 220. For example, if distance 220 is 2 mm, distance 222 can be 3.5 mm.

In some examples, reducing distance 222 can improve clinical outcomes. For example, when distance 222 is minimized, the user can determine tissue and/or organs will be cut close to the distal end 220 of the second elongated member 209. Accordingly, the user can more accurately cut tissue and/or organs and avoid cutting the wrong tissue and/or organs.

The second slot of the first elongated member 207 can have similar or the same dimensions as the first slot 218. For example, the distal end 210 of the first slot 218 can be less than 1 mm from a distal end of the second slot when the reloadable cartridge assembly 203 is in the clamped position. Accordingly, a distance between a distal end of the second slot and the distal end 210 of the second elongated member 209 can be equal to distance 222 when the reloadable cartridge assembly 203 is in the clamped position. For example, the distance between the distal end of the second slot and the distal end 210 of the second elongated member 209 can be less than 8 mm when distance 222 is less than 8 mm.

Figure 3:
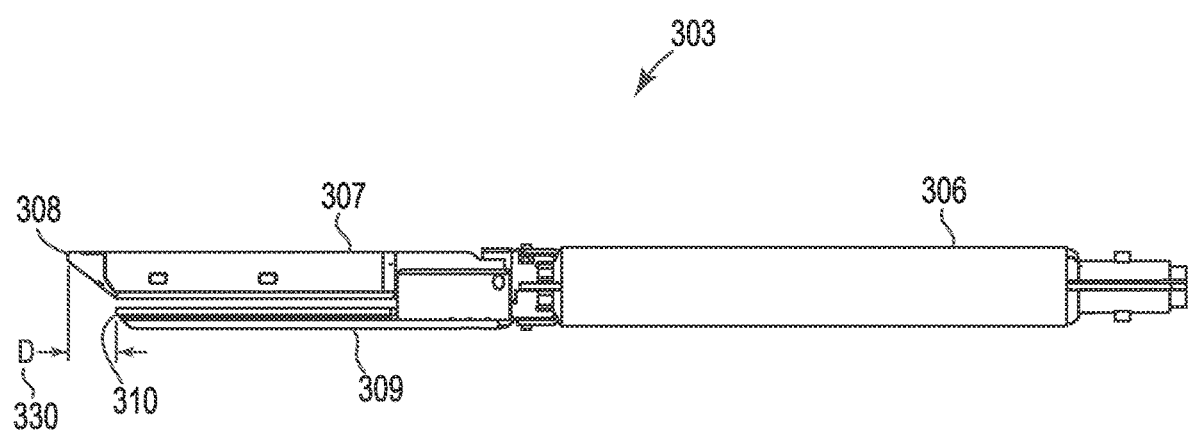
FIG. 3 is a schematic diagram of a reloadable cartridge assembly in a clamped position in accordance with a number of embodiments of the present disclosure.

FIG. 3 is a schematic diagram of a reloadable cartridge assembly 303 in a clamped position in accordance with a number of embodiments of the present disclosure. The reloadable cartridge 303 can include a shaft 306, a first elongated member 307, and a second elongated member 309, as previously described in FIG. 2A.

In some examples, a distal end 308 of the first elongated member 307 can be a distance 330 from a distal end 310 of the second elongated member when the reloadable cartridge assembly 303 is in a clamped position. For example, the distal end 308 of the first elongated member 307 can be greater than 9 mm from the distal end 310 of the second elongated member 309 when the reloadable cartridge assembly 303 is in the clamped position.

Increasing the distance 330 between the distal end 308 of the first elongated member 307 and the distal end 310 of the second elongated member when the reloadable cartridge assembly 303 is in the clamped position can reduce damage to adjacent tissue and/or organs. For example, to properly place a number staples at a desired location in a body, a user may need to get close to and/or contact adjacent tissue and/or organs of the patient. The user can use the distal end 308 of the elongated member 308 to push away tissue and/or organs from the second elongated member 309 to prevent clamping, stapling, and/or cutting the wrong tissue and/or organs.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A reloadable cartridge assembly apparatus, comprising:
a first elongated member including a staple cartridge configured to eject a number of staples; and
a second elongated member pivotally coupled to the first elongated member, wherein the second elongated member includes a number of pockets configured to receive and form the number of staples ejected from the staple cartridge, and wherein a furthest distal pocket of the number of pockets is less than 6 millimeters (mm) from a distal end of the second elongated member and a distal end of the first elongated member is greater than 9 mm from the distal end of the second elongated member in response to the reloadable cartridge assembly being in a clamped position, and wherein the distal end of the first elongated member is greater than 9 mm from the distal end of the second elongated member to push away adjacent tissue or an adjacent organ from the second elongated member to prevent at least one of: clamping, stapling, or cutting of the adjacent tissue or the adjacent organ.

2. The apparatus of claim 1, wherein the distal end of the second elongated member is blunt.

3. The apparatus of claim 1, wherein the first elongated member further comprises a mechanism configured to eject the number of staples.

4. The apparatus of claim 1, wherein the second elongated member includes a number of grooves.

5. The apparatus of claim 4, wherein a groove of the number of grooves creates an opening from a first pocket to a second pocket.

6. The apparatus of claim 5, wherein the first pocket is configured to receive a first portion of a staple of the number of staples, the second pocket is configured to receive a second portion of the staple, and the groove is configured to receive and fold the first and second portion of the staple.

7. A reloadable cartridge assembly, comprising:
a first elongated member including a staple cartridge configured to eject a number of staples; and
a second elongated member pivotally coupled to the first elongated member, wherein the second elongated member includes a first slot configured to receive a blade, and wherein a distal end of the first slot is less than 8 millimeters (mm) from a distal end of the second elongated member and a distal end of the first elongated member is greater than 9 mm from the distal end of the second elongated member in response to the reloadable cartridge assembly being in a clamped position, and wherein the distal end of the first elongated member is greater than 9 mm from the distal end of the second elongated member to push away adjacent tissue or an adjacent organ from the second elongated member to prevent at least one of: clamping, stapling, or cutting of the adjacent tissue or the adjacent organ.

8. The apparatus of claim 7, wherein the staple cartridge is configured to eject the number of staples when the reloadable cartridge assembly is in a clamped position.

9. The apparatus of claim 8, wherein the first elongated member includes a second slot configured to receive the blade when the reloadable cartridge assembly is in the clamped position.

10. The apparatus of claim 9, wherein the distal end of the first slot is less than 1 mm from a distal end of the second slot when the reloadable cartridge assembly is in the clamped position.

11. The apparatus of claim 9, wherein a distal end of the second slot is less than 8 mm from the distal end of the second elongated member when the reloadable cartridge assembly is in the clamped position.

12. The apparatus of claim 8, wherein the reloadable cartridge assembly is configured to clamp tissue between the first elongated member and the second elongated member when the reloadable cartridge assembly is in the clamped position.

13. The apparatus of claim 7, wherein the reloadable cartridge assembly is configured to receive tissue between the first elongated member and the second elongated member when the reloadable cartridge assembly is in an unclamped position.

14. A reloadable cartridge assembly, comprising:
a first elongated member including a staple cartridge configured to eject a number of staples when the reloadable cartridge assembly is in a clamped position; and
a second elongated member pivotally coupled to the first elongated member, wherein the second elongated member includes a number of pockets configured to receive and form the number of staples ejected from the staple cartridge, and wherein a furthest distal pocket of the number of pockets is less than 6 millimeters (mm) from a distal end of the second elongated member and a distal end of the first elongated member is greater than 9 millimeters (mm) from the distal end of the second elongated member in response to the reloadable cartridge assembly being in the clamped position, and wherein the distal end of the first elongated member is greater than 9 mm from the distal end of the second elongated member to push away adjacent tissue or an adjacent organ from the second elongated member to prevent at least one of: clamping, stapling, or cutting of the adjacent tissue or the adjacent organ.

15. The apparatus of claim 14, wherein the first elongated member is proximate to the second elongated member in response to the reloadable cartridge assembly being in the clamped position.

16. The apparatus of claim 14, wherein the first elongated member is blunt.

17. The apparatus of claim 14, wherein a proximal end of the first elongated member is pivotally coupled to a proximal end of the second elongated member.

18. The apparatus of claim 14, further comprising a shaft, wherein the first elongated member and the second elongated member are coupled to the shaft.

19. The apparatus of claim 18, wherein the reloadable cartridge assembly is coupled to a surgical handle assembly via the shaft.

20. The apparatus of claim 19, wherein the reloadable cartridge assembly is in the clamped position in response to a movable handle member of the surgical handle assembly being actuated in a proximal direction.

\* \* \* \* \*